United States Patent
Kumar Karn et al.

(10) Patent No.: US 12,362,049 B2
(45) Date of Patent: Jul. 15, 2025

(54) DIFFERENTIABLE MULTI-AGENT ACTOR-CRITIC FOR MULTI-STEP RADIOLOGY REPORT SUMMARIZATION SYSTEM

(71) Applicant: SIEMENS HEALTHINEERS AG, Forchheim (DE)

(72) Inventors: Sanjeev Kumar Karn, Plainsboro, NJ (US); Oladimeji Farri, Upper Saddle River, NJ (US)

(73) Assignee: Siemens Healthineers AG, Forchheim (DE)

( * ) Notice: Subject to any disclaimer, the term of this patent is extended or adjusted under 35 U.S.C. 154(b) by 732 days.

(21) Appl. No.: 17/661,946

(22) Filed: May 4, 2022

(65) Prior Publication Data

US 2022/0374584 A1 Nov. 24, 2022

Related U.S. Application Data

(60) Provisional application No. 63/186,246, filed on May 10, 2021.

(51) Int. Cl.
| | |
|---|---|
| *G16H 15/00* | (2018.01) |
| *G06F 40/216* | (2020.01) |
| *G06N 3/084* | (2023.01) |
| *G06N 3/092* | (2023.01) |

(52) U.S. Cl.
CPC .............. *G16H 15/00* (2018.01); *G06N 3/084* (2013.01); *G06N 3/092* (2023.01); *G06F 40/216* (2020.01)

(58) Field of Classification Search
CPC ........ G16H 15/00; G06N 3/084; G06N 3/092; G06F 40/216
See application file for complete search history.

(56) References Cited

U.S. PATENT DOCUMENTS

| | | | | |
|---|---|---|---|---|
| 11,197,036 | B2 * | 12/2021 | Chao | ..................... G06F 16/745 |
| 2022/0375210 | A1 * | 11/2022 | Ngo | .......................... G06T 7/70 |
| 2024/0347156 | A1 * | 10/2024 | Paulett | .................. G16H 10/60 |

OTHER PUBLICATIONS

Jacob Devlin, Ming-Wei Chang, Kenton Lee, and Kristina Toutanova. 2018. Bert: Pre-training of deep bidirectional transformers for language understanding. arXiv preprint arXiv:1810.04805.
N Reed Dunnick and Curtis P Langlotz. 2008. The radiology report of the future: a summary of the 2007 Intersociety conference. Journal of the American College of Radiology, 5(5):626-629.
Günes Erkan and Dragomir R. Radev. 2011. Lexrank: Graph-based lexical centrality as salience in text summarization. CoRR, abs/1109.2128.
Jakob Foerster, Gregory Farquhar, Triantafyllos Afouras, Nantas Nardelli, and Shimon Whiteson. 2018. Counterfactual multi-agent policy gradients. In Proceedings of the AAAI Conference on Artificial Intelligence, vol. 32.
Jakob N Foerster, Yannis M Assael, Nando De Freitas, and Shimon Whiteson. 2016. Learning to communicate with deep multi-agent reinforcement learning. arXiv preprint arXiv:1605.06676.

(Continued)

*Primary Examiner* — Etienne P Leroux

(57) ABSTRACT

Systems and methods for using a differentiable multi-agent Actor-Critic (DiMAC) for multi-step radiology report summarization. The tasks of extracting salient sentences and phrases are divided across two collaborating agents that are trained end-to-end using reinforcement learning (RL).

20 Claims, 9 Drawing Sheets

(56) References Cited

OTHER PUBLICATIONS

Kilem Li Gwet. 2008. Computing inter-rater reliability and its variance in the presence of high agreement. British Journal of Mathematical and Statistical Psychology, 61(1):29-48.
Eduard Hovy, Chin-Yew Lin, et al. 1999. Automated text summarization in summarist. Advances in automatic text summarization, 14:81-94.
Vijay R Konda and John N Tsitsiklis. 2000. Actorcritic algorithms. In Advances in neural information processing systems, pp. 1008-1014. Citeseer.
Landon Kraemer and Bikramjit Banerjee. 2016. Multiagent reinforcement learning as a rehearsal for decentralized planning. Neurocomputing, 190:82-94.
Chin-Yew Lin. 2004. Rouge: A package for automatic evaluation of summaries. In Text Summarization Branches Out, pp. 74-81, Barcelona, Spain. Association for Computational Linguistics.
Tomas Mikolov, Kai Chen, Greg Corrado, and Jeffrey Dean. 2013. Efficient estimation of word representations in vector space. arXiv preprint arXiv:1301.3781.
Igor Mordatch and Pieter Abbeel. 2018. Emergence of grounded compositional language in multi-agent populations. In Thirty-second AAAI conference on artificial intelligence.
Jingbo Shang, Jialu Liu, Meng Jiang, Xiang Ren, Clare R Voss, and Jiawei Han. 2018. Automated phrase mining from massive text corpora. IEEE Transactions on Knowledge and Data Engineering, 30(10):1825-1837.
Sainbayar Sukhbaatar, Rob Fergus, et al. 2016. Learning multiagent communication with backpropagation. Advances in neural information processing systems, 29:2244-2252.
Richard S Sutton, David A McAllester, Satinder P Singh, Yishay Mansour, et al. 1999. Policy gradient methods for reinforcement learning with function approximation. In NIPs, vol. 99, pp. 1057-1063. Citeseer.
Ming Tan. 1993. Multi-agent reinforcement learning: Independent vs. cooperative agents. In Proceedings of the tenth international conference on machine learning, pp. 330-337.
Zheng Tian, Shihao Zou, Ian Davies, Tim Warr, Lisheng Wu, Haitham Bou Ammar, and Jun Wang. 2020. Learning to communicate implicitly by actions. In Proceedings of the AAAI Conference on Artificial Intelligence, vol. 34, pp. 7261-7268.
Ashish Vaswani, Noam Shazeer, Niki Parmar, Jakob Uszkoreit, Llion Jones, Aidan N Gomez, Lukasz Kaiser, and Illia Polosukhin. 2017. Attention is all you need. arXiv preprint arXiv:1706.03762.
Oriol Vinyals, Meire Fortunato, and Navdeep Jaitly. 2015. Pointer networks. In Advances in Neural Information Processing Systems, vol. 28. Curran Associates, Inc.
A Wallis and P McCoubrie. 2011. The radiology report—are we getting the message across? Clinical radiology, 66(11):1015-1022.
Manzil Zaheer, Guru Guruganesh, Avinava Dubey, Joshua Ainslie, Chris Alberti, Santiago Ontanon, Philip Pham, Anirudh Ravula, QifanWang, Li Yang, et al. 2020. Big bird: Transformers for longer sequences. arXiv preprint arXiv:2007.14062.
Jingqing Zhang, Yao Zhao, Mohammad Saleh, and Peter Liu. 2020. Pegasus: Pre-training with extracted gap-sentences for abstractive summarization. In International Conference on Machine Learning, pp. 11328-11339. PMLR.
Yuhao Zhang, Derek Merck, Emily Bao Tsai, Christopher D. Manning, and Curtis P. Langlotz. 2019. Optimizing the factual correctness of a summary: A study of summarizing radiology reports.
Emily Alsentzer, John Murphy, William Boag, Wei-Hung Weng, Di Jin, Tristan Naumann, and Matthew McDermott. 2019. Publicly available clinical BERT embeddings. In Proceedings of the 2nd Clinical Natural Language Processing Workshop, pp. 72-78, Minneapolis, Minnesota, USA. Association for Computational Linguistics.
Yen-Chun Chen and Mohit Bansal. 2018. Fast abstractive summarization with reinforce-selected sentence rewriting. In Proceedings of the 56th Annual Meeting of the Association for Computational Linguistics (vol. 1: Long Papers), pp. 675-686, Melbourne, Australia. Association for Computational Linguistics.
Wan-Ting Hsu, Chieh-Kai Lin, Ming-Ying Lee, Kerui Min, Jing Tang, and Min Sun. 2018. A unified model for extractive and abstractive summarization using inconsistency loss. In Proceedings of the 56th Annual Meeting of the Association for Computational Linguistics (vol. 1: Long Papers), pp. 132-141. Association for Computational Linguistics.
Aishwarya Jadhav and Vaibhav Rajan. 2018. Extractive summarization with Swap-Net: Sentences and words from alternating pointer networks. In Proceedings of the 56th Annual Meeting of the Association for Computational Linguistics (vol. 1: Long Papers), pp. 142-151, Melbourne, Australia. Association for Computational Linguistics.
Mike Lewis, Yinhan Liu, Naman Goyal, Marjan Ghazvininejad, Abdelrahman Mohamed, Omer Levy, Veselin Stoyanov, and Luke Zettlemoyer' 2019. Bart: Denoising sequence-to-sequence pretraining for natural language generation, translation, and comprehension. arXiv preprint arXiv:1910.13461.
Yang Liu and Mirella Lapata. 2019. Text summarization with pretrained encoders. In Proceedings of the 2019 Conference on Empirical Methods in Natural Language Processing and the 9th International Joint Conference on Natural Language Processing (EMNLP-IJCNLP), pp. 3730-3740, Hong Kong, China. Association for Computational Linguistics.
Christopher D. Manning, Mihai Surdeanu, John Bauer, Jenny Finkel, Steven J. Bethard, and David McClosky. 2014. The Stanford CoreNLP natural language processing toolkit. In Association for Computational Linguistics (ACL) System Demonstrations, pp. 55-60.
Abigail See, Peter J. Liu, and Christopher D. Manning. 2017. Get to the point: Summarization with pointergenerator networks. In Proceedings of the 55th Annual Meeting of the Association for Computational Linguistics (vol. 1: Long Papers), pp. 1073-1083, Vancouver, Canada. Association for Computational Linguistics.
Yuhao Zhang, Daisy Yi Ding, Tianpei Qian, Christopher D. Manning, and Curtis P. Langlotz. 2018. Learning to summarize radiology findings. In Proceedings of the Ninth International Workshop on Health Text Mining and Information Analysis, pp. 204-213, Brussels, Belgium. Association for Computational Linguistics.

\* cited by examiner

Algorithm 1 Differentiable Multi-Agent Actor Critic

1: procedure TRAIN-DIMAC
2:  Initialize parameters of actors ($a_w$ and $a_s$), critic ($c$) & communicator ($m$) as $\theta^a = D_{s2s}$, $\theta^w = D_{w2w}$, $\theta^c = D_{w2w}$ & $\theta^m = switch$
3:  for each training episode $i$ do
4:   step $j \leftarrow 1$
5:   while action $u_j^w \neq$ END do
6:    compute actors & critic states
7:    sample actions $u_j^s$ & $u_j^w$
8:    compute rewards $r_j^s$ & $r_j^w$ for $u_j^s$ & $u_j^w$
9:    compute message $m_j$ & value function $V_j$
10:   $j \leftarrow j+1$
11:  compute global reward $r^g$
12:  for $j = t$ to $1$ do
13:   compute discounted reward $G_j^s$ and $G_j^w$
14:   estimate action-value functions $Q_j^s$ & $Q_j^w$
15:   compute advantages $A_j^s$ & $A_j^w$
16:   accumulate critic gradient $\Delta\theta^c$
17:   accumulate actor gradients $\Delta\theta^s$ & $\Delta\theta^w$
18:  update critic $\theta^c_{i+1} = \theta^c_i - \alpha\Delta\theta^c$
19:  update actors as $\theta^s_{i+1} = \theta^s_i + \alpha\Delta\theta^s$ & $\theta^w_{i+1} = \theta^w_i + \alpha\Delta\theta^w$
20:  return $\theta^s$, $\theta^w$ & $\theta^c$

Notations

| General | | MLE | | RL | |
|---|---|---|---|---|---|
| $f$ | FINDINGS | $E$ | encoder network | $a$ | agent (actors) |
| $I$ | IMPRESSIONS | $D$ | pointer network | $c$ | critic |
| $K$ | Keywords | $w2w$ | word LSTM | $u$ | action |
| $w$ | word | $s2s$ | sentence LSTM | $m$ | message value |
| $s$ | sentence | $a$ | attention score | $r$ | reward |
| $p$ | position | $c$ | context vector | $G$ | discounted reward |
| $m$ | total words | $v$ | trainable vector | $V$ | value function |
| $n$ | total sentences | $q$ | switch value | $Q$ | action value function |
| $h$ | hidden vector | $W$ | trainable matrix | $A$ | advantage function |
| $y$ | train label | $Conv$ | CNN network | | |

FIG. 6

Algorithm 2 Policy Pretraining Algorithm

1: procedure TRAIN-JOINT-EXTRACTORS($F, I, P$)
2:     *Randomly Initialize:* $E_{w2x}, E_{x2x}, P_{w2x}, P_{x2x}$ & *switch*
3:     for $k = 1$ to $|F|$ do
4:         $\{h_1^{E_{w2x}}, \ldots, h_n^{E_{w2x}}\} \leftarrow E_{w2x}(F_k)$
5:         $\{h_1^{E_{x2x}}, \ldots, h_n^{E_{x2x}}\} \leftarrow E_{x2x}(F_k)$
6:         $Loss \leftarrow Array()$
7:         $h_0^{P_{w2x}}, h_0^{P_{x2x}} \leftarrow h_n^{E_{w2x}}, h_n^{E_{x2x}}$
8:         for $j = 1$ to $t$ do
9:             $\{a_{1j}^w, \ldots\} \leftarrow Attn(h_{j-1}^{P_{w2x}}, \{h_i^{E_{w2x}}, \ldots\})$
10:             $c_j^w \leftarrow \sum_{i=1}^{n} a_{ij}^w \times h_i^{E_{w2x}}$
11:             $h_j^{P_{w2x}} \leftarrow P_{w2x}(h_{j-1}^{P_{w2x}}, c_j^w)$
12:             $\{a_{1j}^x, \ldots\} \leftarrow Attn(h_{j-1}^{P_{x2x}}, \{h_i^{E_{x2x}}, \ldots\})$
13:             $c_j^x \leftarrow \sum_{i=1}^{n} a_{ij}^x \times h_i^{E_{x2x}}$
14:             $h_j^{P_{x2x}} \leftarrow P_{x2x}(h_{j-1}^{P_{x2x}}, c_j^x)$
15:             $q_j \leftarrow switch(h_j^{P_{w2x}}, c_j^w, h_j^{P_{x2x}}, c_j^x)$
16:             $p_j^w \leftarrow \arg\max(\{a_{1j}^w, \ldots\})$
17:             $p_j^x \leftarrow \arg\max(\{a_{1j}^x, \ldots\})$
18:             $\hat{q}_j \leftarrow step(q_j)$
19:             $Loss.\text{ADD}(-\log(\hat{q}_j \times p_j^w + (1-\hat{q}_j) \times p_j^x) - \log q_j)$
20:         update $E_{w2x}, E_{x2x}, P_{w2x}, P_{x2x}$ and *switch*
21:     return $E_{w2x}, E_{x2x}, P_{w2x}, P_{x2x}$ & *switch*

FIG. 7

DIFFERENTIABLE MULTI-AGENT ACTOR-CRITIC FOR MULTI-STEP RADIOLOGY REPORT SUMMARIZATION SYSTEM

CROSS REFERENCE TO RELATED APPLICATIONS

This patent document claims the benefit of the filing date under 35 U.S.C. § 119(e) of U.S. Provisional Patent Application Ser. No. 63/186,246 filed on May 10, 2021, which is hereby incorporated in its entirety by reference.

FIELD

The present embodiments relate to automatic summarization of a radiology report.

BACKGROUND

Abstractive text summarization is the task of generating a concise summary that captures the salient ideas of the source text. Automatic summarization is especially significant for radiology reports since it alleviates the burden of reading through the lengthy and obscure reports in order to quickly and efficiently understand the contents therein. Asides aiding efficient consumption of the radiologist's reasoning and conclusion, the summarization and resulting summary assists the referring physician to explain, confirm, or exclude differential diagnoses. Manual summarization may require years of training to accumulate enough expertise to write concise and informative radiology report summarization and may differ in styles and formats between doctors and clinicians. Automatically generating accurate summaries from clinical reports may save time, improve summary coverage, and reduce errors.

Automatically generating an abstractive summary of information-rich text like radiology reports involves multiple tasks, for example at least acquisition of salient content and generation of a concise, easily consumable impression from the salient content. Many recent radiology report summarization research into automatization has focused on single-step end-to-end modelling that subsume the underlying tasks of salient content acquisition. However, the main disadvantage of such single step end-to-end systems are lack of explainability and require large number of labeled examples for training. As an alternative approach, two-step end-to-end systems were proposed. These two step end-to-end systems initially train extractive and abstractive systems separately and then use the extractive system as an agent in a single agent reinforcement learning (RL) setup with the abstractive system as part of the environment. The extractive system extracts salient sentences, and the abstractive system paraphrases these sentences to produce a summary. This summary is in turn used to compute a reward for the RL training. However, this single-agent setup or two-step with a single extractive process often fails to extract some salient sentences, or it extracts irrelevant ones, leading to the generation of incomplete/incorrect summarization.

SUMMARY

In a first aspect, a system is provided for multi-step radiology report summarization. The system includes a word extraction network, a sentence extraction network, and an abstractor network. The word extraction network is configured to extract one or more words from a radiology report. The sentence extraction network is configured to extract one or more salient sentences from the radiology report based at least in part on the extracted one or more words. The abstractor network is configured to condense one or more of the one or more extracted salient sentences into a concise summary of the radiology report. The word extraction network, the sentence extraction network, and the abstractor network are trained end to end using at least a critic and a communication channel, wherein the critic is configured to estimate a value function that is used to compute a policy gradient for the word extraction network and the sentence extraction network, and the communication channel is configured to pass gradient information between the word extraction network and the sentence extraction network.

In an embodiment, the word extraction network and the sentence extraction network comprise a bi-directional LSTM based word encoder and a bi-directional LSTM sentence encoder respectively. The bi-directional LSTM based word encoder is configured to obtain word representations from a FINDINGS portion of the radiology report and the bi-directional LSTM sentence encoder is configured to obtain sentence representations. In an embodiment, the abstractor network comprises a pointer generator network.

In an embodiment, during training, the word extraction network and sentence extraction network are configured using multiple agent reinforcement learning. In an embodiment, the word extraction network and sentence extraction network actions at a previous step are input into the communication channel that generates a sigmoidal, mt, that is input into the sentence extraction network wherein 1−mt is input into the word extraction network. In an embodiment, during training, when the word extraction network or the sentence extraction network selects an action, a reward is provided to the word extraction network or the sentence extraction network based on an individual reward function computed specifically for either the word extraction network or the sentence extraction network. The reward for the sentence extraction network is computed using ROUGE L recall by comparing extracted salient sentences and condensed salient sentences with ground truth data. The reward for the word extraction network is computed by checking if an extracted word is in a given set of keywords.

In an embodiment, the system further comprises an output interface configured to provide the concise summary to a user.

In a second aspect, a method is provided for configuring a system for multi-step radiology report summarization, wherein the system comprises at least a sentence extraction network, a word extraction network, a critic network, and a communication channel, the method comprising: computing states for the sentence extraction network, the word extraction network, and the critic network; inputting training data from a FINDINGS section of a radiology report to the sentence extraction network and the word extraction network; sampling actions by the sentence extraction network and the word extraction network; computing rewards based on the actions and the states; and updating the sentence extraction network, the word extraction network, and the critic network based on the computed rewards.

Computing, sampling, computing, and updated is iteratively performed for a plurality of iterations. For Sampling actions by the sentence extraction network and the word extraction network, only one of the sentence extraction network or the word extraction network is active while the other is paused. In an embodiment, each of the sentence extraction network and the word extraction network selects one of its actions and communicates with the other respective network at every step. In an embodiment, the communication channel is configured to generate a sigmoidal, mt, that is input into the sentence extraction network, wherein 1−mt is input into the word extraction network.

The word extraction network is configured to extract one or more words from the FINDINGS section based on a list of keywords. The sentence extraction network is configured to extract one or more sentences from the FINDINGS section based in part on the extracted one or more words.

In a third aspect, a method is provided for automatic summarization of a FINDINGS section of a radiology report, the method comprising: acquiring a radiology report that describes results of a medical procedure; inputting the FINDINGS section of the radiology report into an automatic summarization system comprising at least a word extraction network, a sentence extraction network, a communications channel, and an abstractor, wherein the automatic summarization system is trained using differential Multi-agent Actor-Critic reinforcement learning; outputting, by the automatic summarization system, an IMPRESSIONS section for the radiology report; and presenting the IMPRESSIONS section to a user.

In an embodiment, the word extraction network is configured to extract one or more words from the FINDINGS section based on a list of keywords. The sentence extraction network is configured to extract one or more sentences from the FINDINGS section based in part on the extracted one or more words. The communications channel is configured to pass information between the word extraction network and the sentence extraction network.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

FIG. 6 depicts an example algorithm for training the two-step summarization framework according to an embodiment.

FIG. 7 depicts an example algorithm for pre-training joint extractors according to an embodiment.

DETAILED DESCRIPTION

Embodiments provide systems and methods for an automatic radiology report summarization system. Embodiments provide a summarization system that leverages core concepts via keywords, refines the extracted words, and makes the extracted words the basis for more fine-grained explainability. Embodiments use a multi-agent reinforcement learning based extractive component for a two-step summarization framework and a Differentiable Multi-agent Actor-Critic (Di-MAC) with independent actors leveraging a communication channel for cooperation. The use of the Di-MAC provides more precise and accurate summaries compared to single-step and to two-step with-single-extractive-processes.

Figure 1:
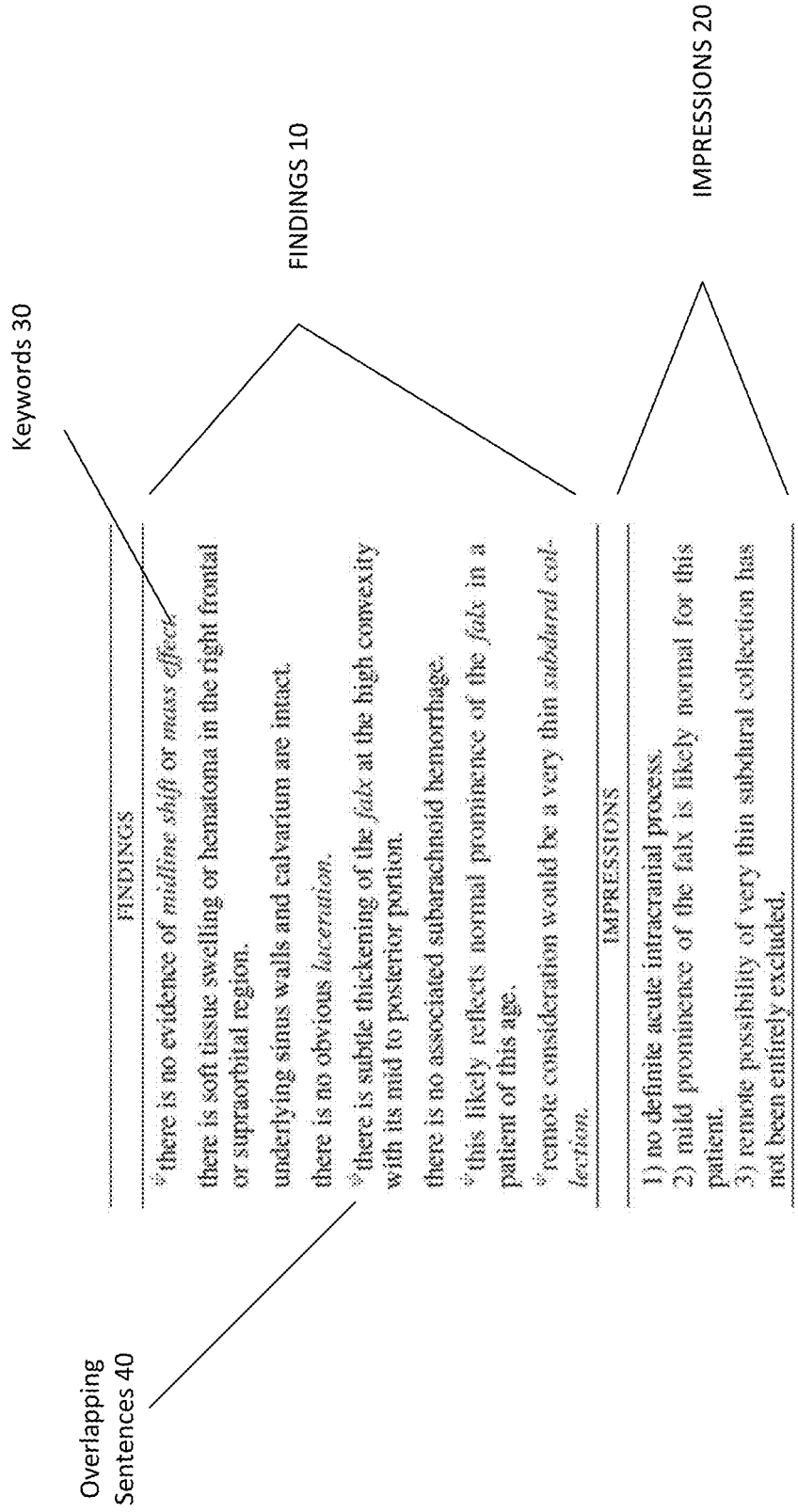
FIG. 1 depicts an example radiology report.

Radiology is a branch of medicine that uses imaging technology to diagnose and treat disease. A radiology report is the formal documentation and communication of the results of a radiologic study or procedure. A radiology report is typically generated by a trained radiologist and may vary greatly in style, format, and effectiveness. Typically, a radiology report includes at least a findings section that includes a comprehensive description of all abnormalities that are relevant to the clinical request or suspected pathology. Radiology reports also include a summary or impression statement that communicates conclusions made about the findings, and suggestions for the referring physician. Findings are often lengthy and information rich. However, a survey of the attitudes of referring physicians shows that the Finding section may be overlooked in favor of only reading the provided summary or impressions section. Thus, the impression may be the only part of the report that is read and needs to accurately reflect the report as a whole including the important/salient information provided in the Findings section. FIG. 1 depicts an example of the findings 10 and impressions 20 sections of a radiology report. FIG. 1 includes FINDINGS 10 (top) and IMPRESSIONS 20 (bottom) sections of a radiologist's report. The symbol w indicates a sentence 40 in FINDINGS that overlaps with sentences in IMPRESSIONS. Italicized words in FINDINGS are core concepts/keywords 30 (e.g., disorder and procedure) that assist in answering clinical questions. The radiology report may be longer, shorter, or include additional sections. The radiology report may be manually generated, for example, by a radiologist, or may be automatically generated.

For the systems described herein, the input to the automatic summarization includes at least the FINDING section and the output of the automatic summarization is a generated IMPRESSIONS section. It is important that the IMPRESSIONS section accurately and comprehensively covers the FINDING section as referring physicians may rely primarily on its contents. Automatic systems have been used in the past for abstractive summarization. For example, in a known two-stage abstractive summarization approach, first an extractive summarization training is performed, and in the next step, the trained encoder out of the extractive summarization is used in an end to end abstractive summarization training. One method trains extractive and abstractive systems separately and then use the extractive system as an agent in a single-agent RL setup with the abstractive system as part of the environment. The extractive system extracts salient sentences and then the abstractive system paraphrases them to arrive at a summary, which in turn is used to compute the reward that drives the RL training.

Reinforcement learning (RL) is a machine learning technique that uses an agent/actor that performs actions. The agent learns to improve the actions (or select better actions) using a reward structure that "reinforces" good behavior. In an example, a RL system represents an environment as a Markov Decision Process (MDP) with specified state space, action space, reward function, and probabilistic transition function. An agent's goal is to learn a policy that maximizes the expected discounted reward characterized by the MDP. Another aspect of RL uses an actor/critic configuration. The actor performs actions that are then judged by the critic. RL applies actor-critic learning using a combination of policy learning and value learning. During training, the actor decides which action should be taken and the critic tells the actor how good (or valuable) the action was and how the actor should adjust based on a policy gradient approach provided by the critic. The policy evaluates the action produced by the actor by computing a value function. In this example, the policy dictates which action to perform. The value function tracks whether the actor is ahead or behind after each action eventually leading to a final outcome. The feedback guides the training process. The actor takes as input the state and outputs the best action. It essentially controls how the actor behaves by learning the optimal policy (policy-based). The critic, on the other hand, evaluates the action by computing the value function (value based). The two networks (actor/critic) both get better in their own role as the time passes. The result is that the overall architecture will learn more efficiently than the two methods separately. The actor may be a neural network with a goal of producing or estimating the best action for a given state. The critic may be another network that receives as input the environment and the action by the actor, concatenates them and output an action value (e.g., Q-value) for the given pair.

Multiagent reinforcement learning (MARL) includes multiple agents or actors. MARL requires that an agent coordinate with other agents to achieve a desired goal. There are different protocols that may be used for MARL training, such as sharing parameters between agents and explicit or implicit communication between agents by using an actor-critic policy gradient with a centralized critic for all agents. The aim of these protocols is to correctly assign credits so that an agent can deduce its contribution to the team's success.

Embodiments provided herein use RL, actor-critic training, and MARL to provide a two-step summarization system that takes the FINDINGS section of a radiology report (consisting of a sequence of sentences) and a set of keywords as input and produces an IMPRESSIONS section (consisting of a sequence of sentences).

Figure 2:
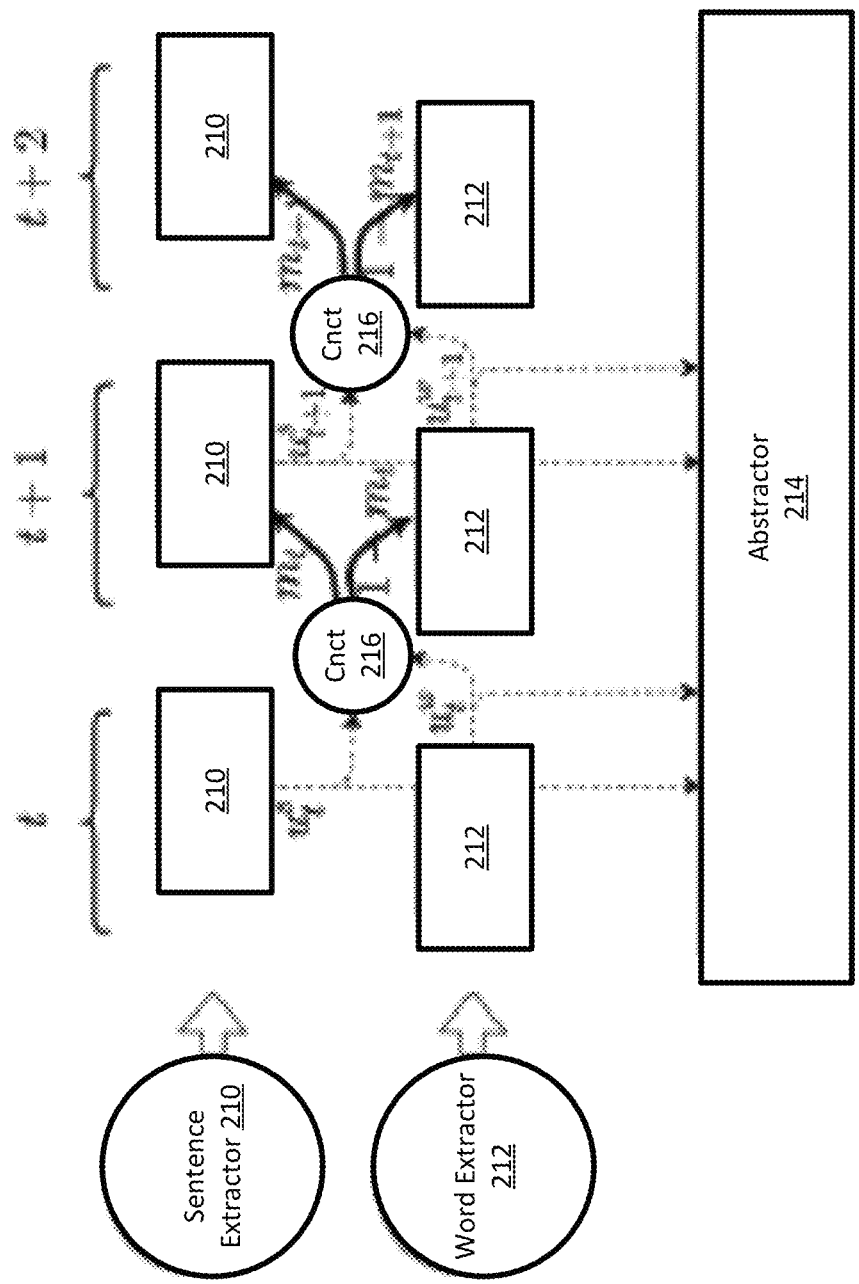
FIG. 2 depicts an example multi-agent extraction system according to an embodiment.

FIG. 2 depicts an example of the of the components of the two-step summarization system according to an embodiment. FIG. 2 includes two distinct actors/agents (a sentence extraction network 210 and a word extraction network 212), an abstractor 214, and a communication channel/connector (cnct) 216. The word extraction network 212 is configured to extract one or more words from a radiology report. The sentence extraction network 210 is configured to extract one or more salient sentences from a radiology report based at least in part of the extracted one or more words. The communication channel is configured to pass information between the word extraction network 212 and the sentence extraction network 210. The abstractor network is configured to condense one or more of the extracted sentences into a concise summary of the radiology report. The word extraction network 212, sentence extraction network 210, and abstractor network are trained end to end using at least a critic configured to estimate a gradient. The critic (not depicted) is used during training to judge or criticize the actions of the actors.

FIG. 2 depicts several actions performed at steps t, t+1, and t+2. The action space at each step of decoding includes extracting a salient sentence, ust and salient word, uwt, for the sentence extraction network 210 and word extraction network 212 respectively. Owing to the communication between the word extraction network 212 and sentence extraction network 210 there is a strong relationship between generated words and sentences. More specifically, sentences with many salient words are more likely to get extracted, and thereby yielding meaningful impression of the findings after the abstractor rewrites the extracted finding sentences. The connection network, cnct 216, provides the communication by passing messages between the two agents. The agent's actions at the previous step, ust−1 and uwt−1, are input to cnct 216 and a sigmoidal, mt, is obtained. The value mt is input to the sentence agent while 1−mt is input to the word agent.

During training, a gradient term that flows between agents during backpropagation provides a richer training signal, and thereby minimizing the learning effort. During training, after an agent selects an action u·j, a reward r·j is given to the agent based on an individual reward function designed specific to the agent. For the sentence actor, a sentence reward SentR is computed using Rlr (ROUGE L recall) by comparing extracted and condensed sentences with ground truths. In case of the word actor, a word reward, WordR, is computed by checking if extracted word is in a given set of keywords. If present, WordR is assigned a respective value, else it is zero. Additionally, the joint actions of the agents eventually generate a global reward. Not depicted, but used during training, a key component of DiMAC is the centralized critic that is used to estimate the gradient to train both of the actors. As learning is centralized, the critic can condition on all of multi-agent's actions (ust and uwt) and states (hst and hwt), contrarily individual actor conditioning only on its action and state. The critic estimates a value function that is used to compute the policy gradient of an agent.

Figure 3:
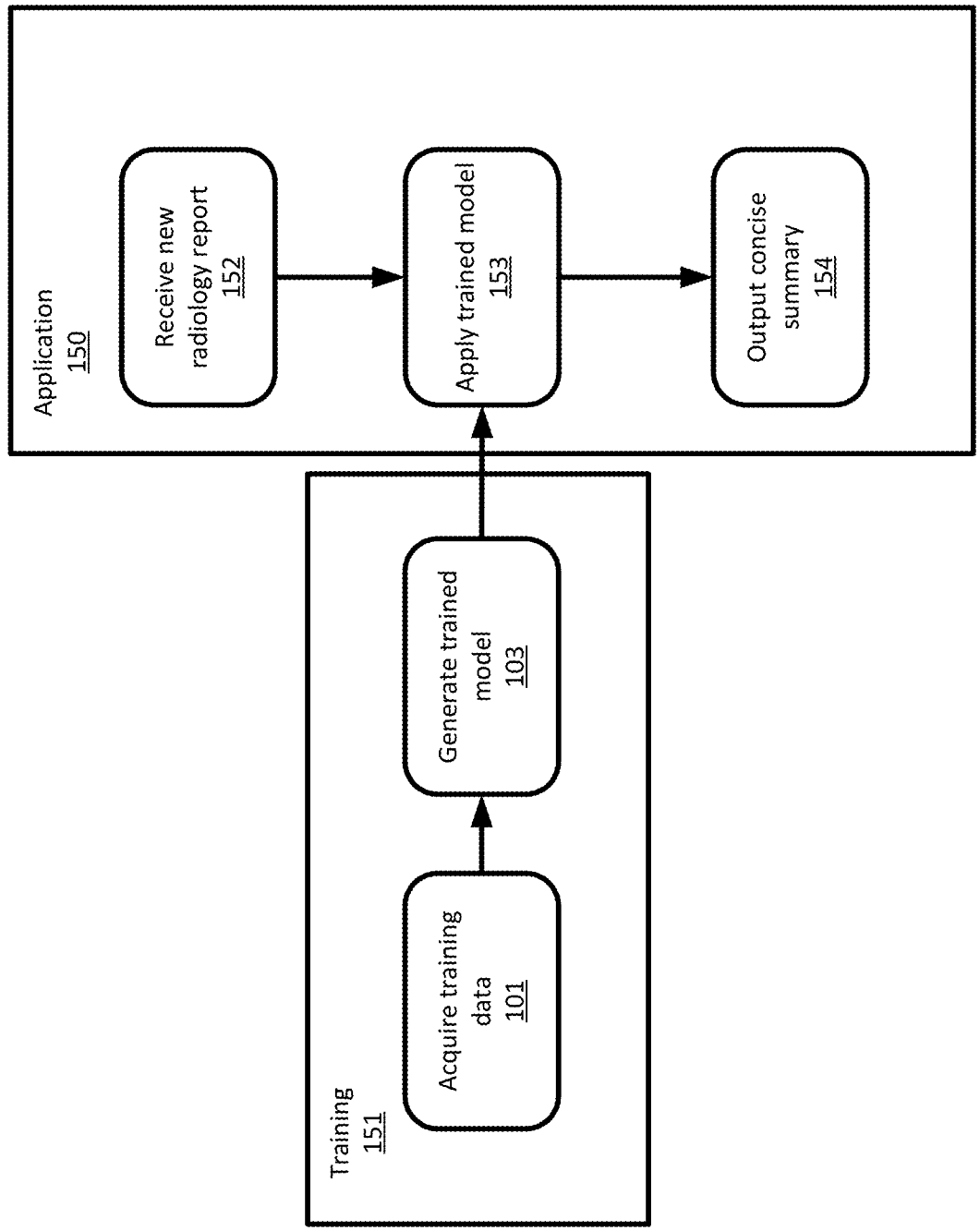
FIG. 3 depicts an example of the training and application of a two-step summarization framework according to an embodiment.

FIG. 3 depicts an example flowchart for training and implementing an automatic radiology summarization system. The flowchart includes two stages, a training stage 151 for generating or training the networks using a collection of training data (labeled data) and an application stage 150 for applying the generated/trained networks to new unseen (unlabeled) data. The training stage 151 includes acquiring 101 training data and inputting the training data into the network(s) in order to generate 103 trained network(s). The training here is performed end-to-end and includes at least the extractors and abstractor 214. The output is trained network(s) that are applied 153 in the application stage 150. The application stage 150 includes acquiring 151 an unseen radiology report, applying 153 the trained networks that were trained during the training stage 151, and outputting 154 a concise summary. The training stage 151 and application stages 150 are described in detail below at FIGS. 5 and 9, respectively. The training stage 151 may be performed at any point prior to the application stage. The training stage 151 may be repeated after new training data is acquired. The application stage 150 may be performed at any point after the training stage 151 generates the trained network(s) and a radiology report is acquired. The application stage 150 may be performed, for example, during (e.g., real time) or directly after a radiological medical procedure is performed or as part of planning for a particular patient once a radiology report has been generated. Alternatively, the application stage 150 may be performed at a later point using medical data or radiology reports acquired and stored, for example, in a PACS or other database.

Figure 4:
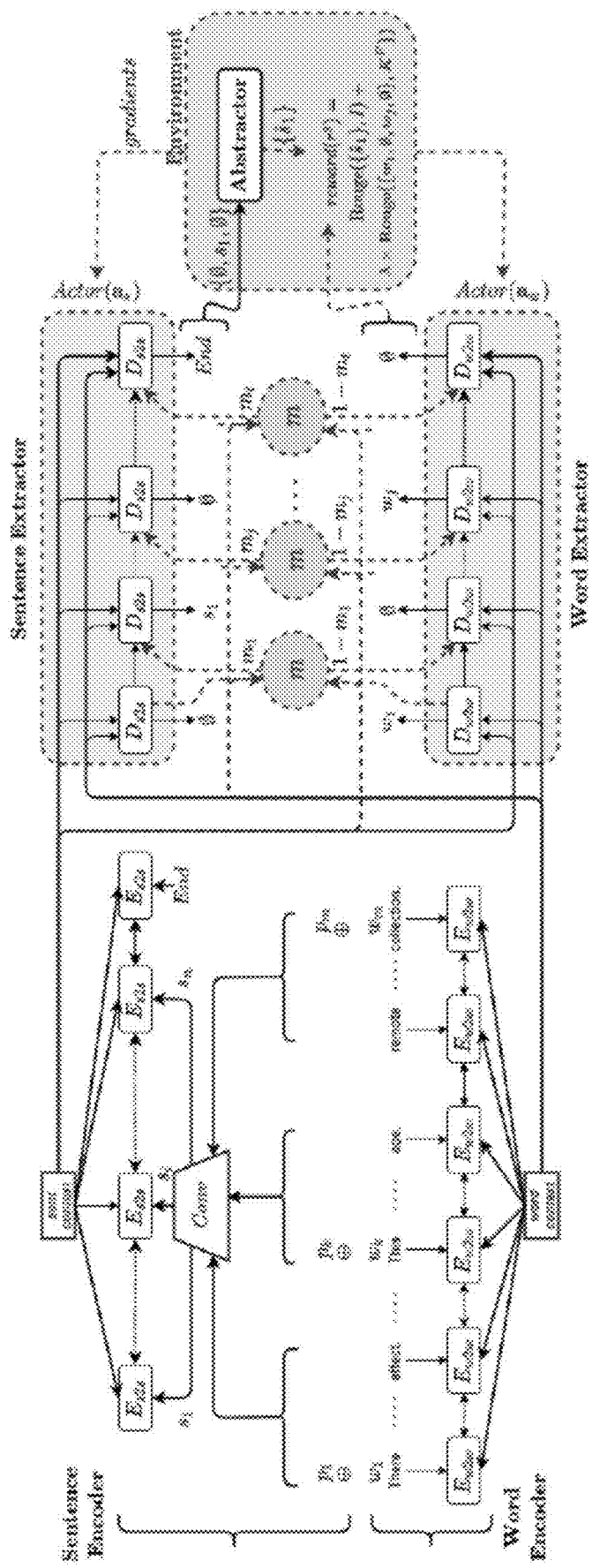
FIG. 4 depicts a two-step summarization framework configured using Differentiable Multi-agent Actor-Critic (Di-MAC) reinforcement learning according to an embodiment.

FIG. 4 depicts a detailed overview of the operation of the two-step summarization framework referred to as DiMAC. The DiMAC components (actors/extractors, communicator (m), environment and communication between them) are indicated by dashed lines and arrows. The first step of the framework includes encoder-extractor networks depicted on the left side including the sentence (Es2s) and word (Ew2w) encoders. These are connected to the extractors on the right side including the sentence (Ds2s) and word (Dw2w) extractors. The word and sentence encoders may be bi-directional LSTMs with word (vw) and sentence (hs) embeddings as input. A convolutional network (Conv) obtains a sentence embedding (hs) from word (vw) and position (vp) embeddings. The extractors are an LSTM pointer network with context vectors as input and either empty (;) or a source position as output at each step. In a second step of the framework, the seq2seq abstractor 214 paraphrases selected sentences. During DiMAC reinforcement learning, the communicator takes contexts and actor hidden states and sends them back messages (m). The critic is not depicted here but plays a role in determining rewards and gradients. Abstracted sentences and selected words are used to compute rewards. As depicted, the system includes encoder networks to encode words and sentences into vector representations. It also includes two pointer extractor networks to determine salient words and sentences by selecting their indices. Both extractor networks run for the same number of steps; however, at each step, the output index of one extractor network is chosen while the other is set as empty (∅). When the input is ∅, an extractor pauses its activity and guides the other extractor in an optimal direction. The abstractor 214 condenses each selected sentence to a concise summary using a pointer generator network. The abstractor 214 uses a copy mechanism to solve the out-of-vocabulary (OOV) problem and a coverage mechanism to solve the repetition problem. The abstractor 214 is trained using heuristically obtained one-to-one matches between FINDINGS and IMPRESSIONS sentences.

The neural networks 4 of FIG. 3 include bi-directional LSTMs. An LSTM network may be a recurrent neural network that has LSTM cell blocks in place of standard neural network layers. The LSTM network may include a plurality of LSTM layers. In each cell of the LSTM network there may be four gates: input, modulation, forget and output gates. The gates determine whether or not to let new input in (input gate), delete the information because the information isn't important (forget gate) or to let the information impact the output at the current time step (output gate). The state of the cell is modified by the forget gate and adjusted by the modulation gate.

Each LSTM cell take an input that is concatenated to the previous output from the cell $h\_(t-1)$. The combined input is squashed via a tanh layer. The input is passed through an input gate. An input gate is a layer of sigmoid activated nodes whose output is multiplied by the squashed input. The input gate sigmoids may ignore any elements of the input vector that aren't required. A sigmoid function outputs values between 0 and 1. The weights connecting the input to these nodes may be trained to output values close to zero to "switch off" certain input values (or, conversely, outputs close to 1 to "pass through" other values). A state variable lagged one time step i.e. $s\_(t-1)$ is added to the input data to create an effective layer of recurrence. A recurrence loop is controlled by a forget gate—that functions similar to the input gate, but instead assists the network learn which state variables should be "remembered" or "forgotten." Alternative structures may be used for LSTM cells or the LSTM network structure.

A convolutional network (Conv) is also used that obtains a sentence embedding (hs) from word (vw) and position (vp) embeddings. The networks, including the convolution network, the encoders, extractors, abstractor 214, critic, etc., as described herein may be defined as a plurality of sequential feature units or layers. The general flow of output feature values may be from one layer to input to a next layer. The information from the next layer is fed to a next layer, and so on until the final output. The layers may only feed forward or may be bi-directional, including some feedback to a previous layer. Skip connections may be provided where some information from a layer is feed to a layer beyond the next layer. The nodes of each layer or unit may connect with all or only a sub-set of nodes of a previous and/or subsequent layer or unit. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. Other network arrangements may be used, such as a support vector machine. Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (e.g., including different weights for different areas of the states). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the machine learnt network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

Figure 5:
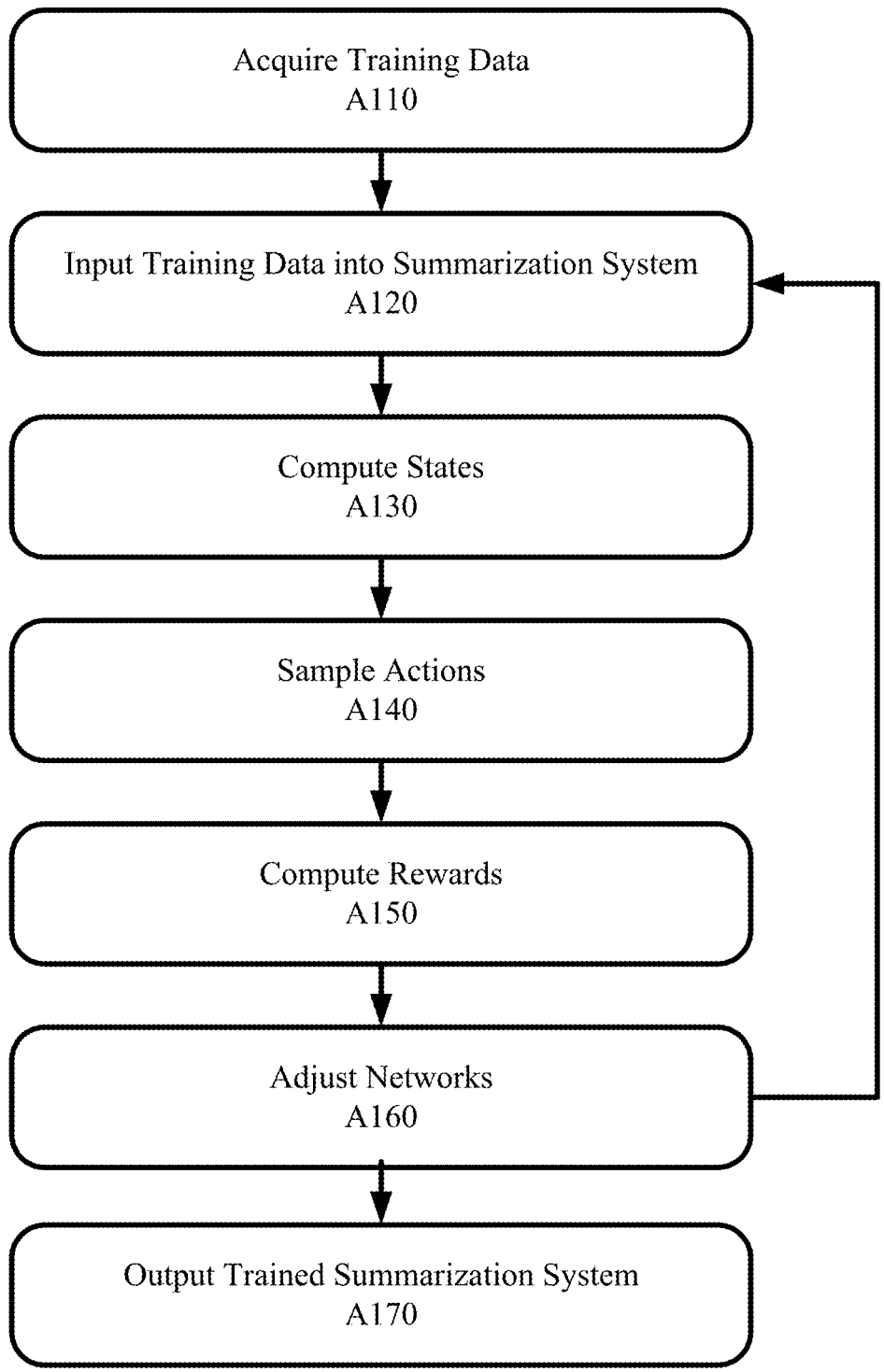
FIG. 5 depicts an example workflow for reinforcement learning according to an embodiment.

FIG. 5 depicts an example flowchart for generating and configuring an automatic two-step summarization system using machine learning, specifically reinforcement learning. Embodiments use a two-step summarization framework that takes the FINDINGS section of a radiology report (consisting of a sequence of sentences) and produces an IMPRESSIONS section (consisting of a sequence of sentences). The network(s) of the two-step summarization system may be trained using a supervised training method. Unlabeled training data is input into the network that generates an outcome that is compared against associated labeled training data. Using backpropagation and one or more gradients, the network(s) adjusts internal parameters based on the comparison. The process is repeated until the network may no longer be improved or a set point is reached. The acts are performed by the system of FIG. 2, 4, 8, other systems, a workstation, a computer, and/or a server. Additional, different, or fewer acts may be provided. The acts are performed in the order shown (e.g., top to bottom) or other orders.

FIG. 6 depicts an example algorithm for the training the DiMAC configured automatic two-step summarization system with a list of notations that may be used in FIG. 6 and the descriptions above and below. FIG. 7 depicts an example algorithm for pretraining the extractors including the training of word encoder (Ew2w), sentence convolutional network (Conv), sentence encoder (Es2s), word extractor (Dw2w), sentence extractor (Ds2s) and switch network (switch). These networks may be trained prior to the end-to-end training of the entire DiMAC configured automatic two-step summarization system. These two algorithms and others may be used to configure the automatic summarization system. Alternative algorithms, steps, or equations may be used.

At act A110, training data is acquired. Training data may include ground truth data or gold standard data. Ground truth data and gold standard data is data that includes correct or reasonably accurate labels. Training data may include previously identified and summarized radiology reports. In an example, the training data may be acquired from the MIMIC III database. The data is split into training, validation, and test reports. AutoPhrase may be used to automatically extract all key phrases from the training dataset. AutoPhrase outputs a ranked list of multi-word phrases. Only high-quality phrases may be selected using a threshold. Sentences and phrases in the findings of a report that overlap with the impression and high-quality phrases are respectively used as the ground-truths for training sentence and word extractors. The training data may be acquired at any point prior to inputting the training data into the network. The training data may include volumes of different resolutions or contrast. The training data may be updated after acquiring new data. The updated training data may be used to retrain or update the network.

At Act A120, the training data is input into the DiMAC system. The DiMAC system is configured to extract salient words, extract salient sentences, and select one or more of the salient sentences to generate a concise summary. Parameters for each of a sentence extraction network 210, a word extraction network 212, a critic network, and a communication channel (also referred to as the cnct 216) are initialized. These networks may be trained prior to the end-to-end training of the entire DiMAC configured automatic two-step summarization system.

At Act A130, the summarization system computes states for the sentence extraction network 210, the word extraction network 212, and the critic network. At Act A140, the summarization system samples actions by the sentence extraction network 210 and the word extraction network 212. The word extraction network 212 and the sentence extraction network 210 have action spaces of source words $\{w_1, \ldots, wm\}$ and sentences $\{s_1, \ldots, sn\}$ respectively. At any decoding step j, the word extraction network 212 and the sentence extraction network 210 choose actions, (i.e. source selection) by using policy networks and hidden states. Due to the communication between the word extraction network 212 and the sentence extraction network 210 provided by the cnct 216, there is some correlation in the actions. The cnct 216 passes messages between the actors. Previous hidden states and contexts are input into the communicator which generates a sigmoidal. The sigmoidal value is input into the state of the sentence or word extractors. The gradient of mj flows between actors during backpropagation and provides rich a training signal that minimizes the learning effort.

At Act A150, the summarization system computes rewards based on the actions and the states. After an agent (word extraction network 212/the sentence extraction network 210) selects an action, a reward is given to it based on an individual reward function designed specific to the agent. In the case of the sentence extraction network 210, a sentence reward SentR is computed using Rlr (ROUGE L recall) by comparing extracted and condensed sentences with ground truths. In case of the word extraction network 212, WordR is computed by checking if an extracted word is in a given set of keywords. A global reward is also generated by the joint actions of the actors. The global reward is computed using:

$$r^g = R_{lr}(\text{concat}\{\ldots, f(\hat{y}_j^s), \ldots\}, I) + \lambda R_{lr}(\text{concat}\{\ldots, (\hat{y}_j^w), \ldots\}, W)$$

The function concat concatenates a set of strings to a text. I is a ground-truth multi-sentence impression and W is a ground-truth key phrases. $\lambda$ is the hyper-parameter to adjust contribution of word reward so that overall generated impression drive the success of agent even if there is some sacrifice of word reward.

In addition, for each step, discounted rewards are calculated, action-value functions are estimated, advantages are computed, and gradients are accumulated using MARL. In an example, an actor network chooses an action at each time step and the critic network evaluates the quality or the Q-value of a given input state. As the critic network learns which states are better or worse, the actor uses this information to teach the agent to seek out good states and avoid bad states. The advantage function evaluates if a state is better or worse than expected. If an action is better than expected (the advantage is greater than 0), the actor should perform more of that action. If an action is worse than expected (the advantage is less than 0), the actor should perform the opposite of that action. If an action performs exactly as expected (the advantage equals 0), the actor doesn't learn anything from that action.

The Critic is configured to estimate the value function which is used to compute the policy gradient of an agent using the following equation:

$$g = \mathbb{E}_{h'_{0:inf}, u'_{0:inf}} \left[ \sum_{t=0}^{T} A'_t \nabla_{\theta^{\pi'}} \log \pi'_t \right]$$

$A_t$ is the advantage function. $Q^\pi$ is an action value function.

At Act A160, the sentence extraction network 210, the word extraction network 212, and the critic network are updated based on the computed rewards. Acts A120-A160 may be repeated for a number of iterations until the summarization system can accurately generate concise summarizations of input FINDINGS. At Act A170, the trained automatic two-step summarization system is output for implementation.

Figure 8:
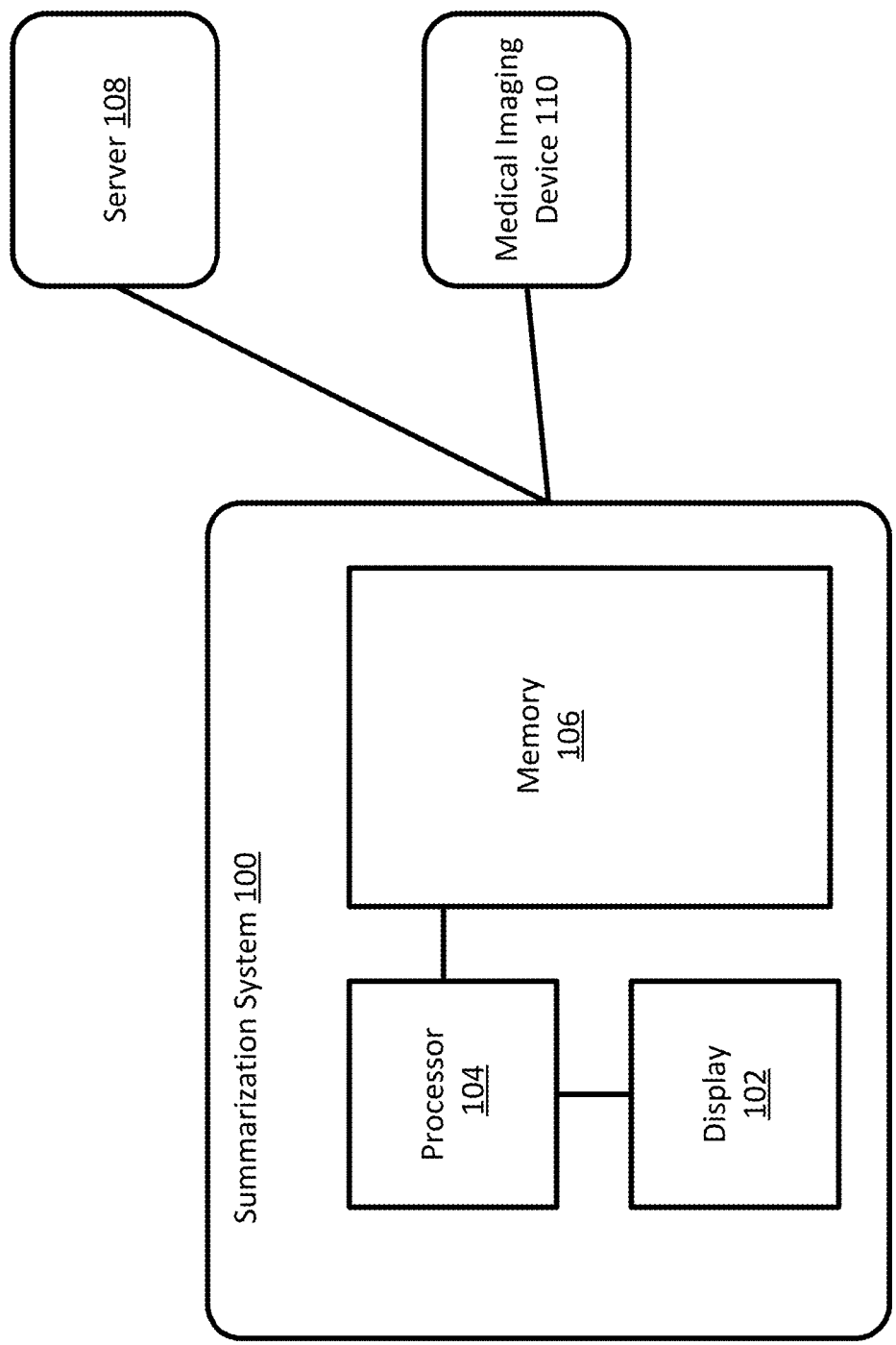
FIG. 8 depicts an example system for implementing a two-step summarization framework configured using Differentiable Multi-agent Actor-Critic (Di-MAC) reinforcement learning according to an embodiment.

FIG. 8 depicts an example system for automatic summarization. The system 100 includes a display 102, a memory 106, and a processor 104. The system may further be in communication with or include a medical imaging device 110 and/or a server 108. A patient may be scanned by the medical imaging device 110. The medical imaging device 110 may be a scanner for one of a medical imaging modalities (e.g., CT scanner, magnetic resonance (MR) scanner, positron emission tomography (PET) scanner, single photon emission computed tomography (SPECT) scanner, ultrasound scanner, x-ray scanner, or other diagnostic imaging scanner 110) and/or a medical therapy system (e.g., x-ray therapy system). Other devices may be used to perform any of the acts. The results of the procedure may be captured or collected into a radiology report, for example, as described in FIG. 1 above. The radiology report may include at least a FINDINGS section.

Figure 9:
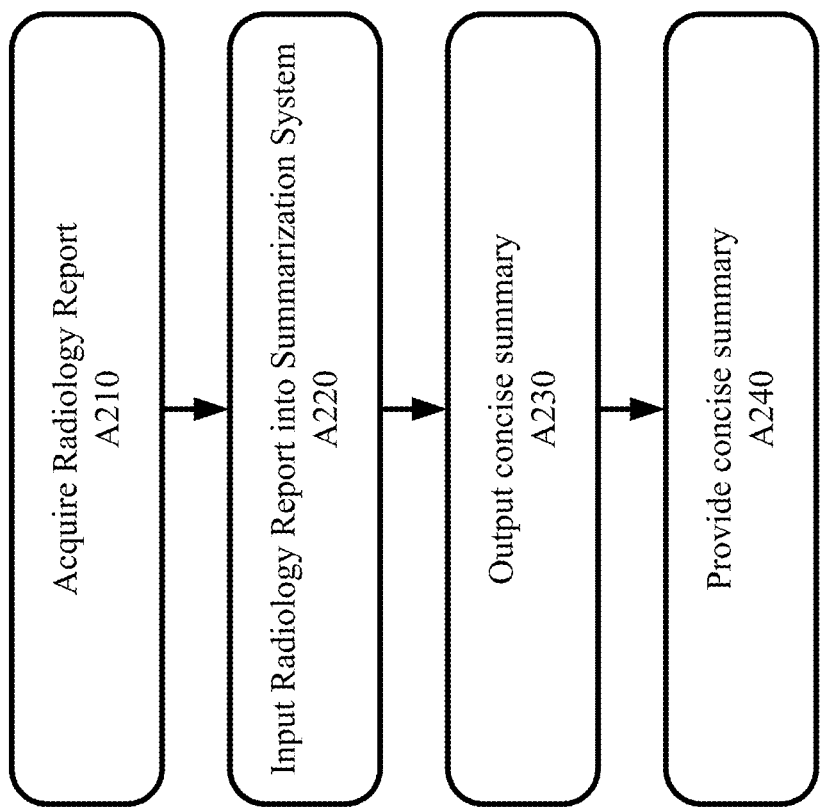
FIG. 9 depicts an example workflow for implementing a two-step summarization framework configured using Differentiable Multi-agent Actor-Critic (Di-MAC) reinforcement learning according to an embodiment.

FIG. 9 is a flow chart diagram of one embodiment of a method for automatic radiology report summarization using the trained summarization system describe above in FIG. 5. The method of FIG. 9 is performed by a system 100, such as the system 100 of FIG. 8. The method of FIG. 9 is performed in the order shown (e.g., top to bottom or numerical), but other orders may be used. The method of FIG. 9 describes the application stage 150 of FIG. 3. The networks as described may already have been pretrained during a training stage 151, for example as described in FIG. 5. Additional, different, or fewer acts may be provided.

At act A210, a medical procedure is performed, and a radiology report is generated. The medical imaging device 110 includes a diagnostic imaging scanner such as CT, MR, PET, or SPECT system or a therapeutic radiation scanner, such as an x-ray or particle therapy system. The diagnostic imaging scanner may be configured to acquire MR images, for example, LGE image data and CINE image data. The diagnostic imaging scanner may alternatively be configured to acquire other types of image data such as 2D/3D ultrasound, as well as 4D CT that includes image data. The diagnostic imaging scanner operates pursuant to one or more settings and scanning parameters to treat or image a patient. The settings and scanning parameters control the location in the patient being scanned, the type of scan (e.g., pulse sequence), and/or radiation dose. The diagnostic imaging scanner is configured by setting values of variables to operate in a particular way appropriate for the particular patient. Once configured by the settings, the medical system treats or images the patient. The diagnostic imaging scanner is configured to generate diagnostic image information. The patient is imaged by the diagnostic imaging scanner using the settings. The radiology report includes at least a FINDINGS section that lists what a radiologist (or other entity) observed or identified in each area of the body in the procedure. The radiologist, for example, may note whether they think an area to be normal, abnormal, or potentially abnormal. The FINDINGS section typically includes short informative phrases describing the pertinent positive and negative observations about a study.

At act A220, the radiology report FINDINGS are input into the automatic summarization system. The automatic summarization system may include one or more instructions or components that are stored in the memory 106 and implemented by the processor 104. The processor 104 may be a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for processing an image. The processor 104 is a single device or multiple devices operating in serial, parallel, or separately. The processor 104 may be a main processor of a computer, such as a laptop or desktop computer, or may be a processor for handling some tasks in a larger system, such as in the medical imaging device 110. The processor 104 is configured by instructions, design, hardware, and/or software to perform the acts discussed herein.

Components and instructions for the automatic summarization system may be stored in the server 108. The server 108 may be co-located with the medical imaging device 110 or may be located remotely. The server 108 may connect to the medical imaging device 110 via a network. The network is a local area, wide area, enterprise, another network, or combinations thereof. In one embodiment, the network is, at least in part, the Internet. Using TCP/IP communications, the network provides for communication between the processor 104 and the server 108. Any format for communications may be used. In other embodiments, dedicated or direct communication is used. The server 108 may include the processor 104 or group of processors. More than one server may be provided. The server 108 is configured by hardware and/or software. In one embodiment, the server 108 performs MARL of the networks using the process described at least in FIG. 5. The server may acquire, and the memory 106 may store the training data including radiology reports.

The processor 104 and/or server 108 are configured to perform the acts discussed above for automatic radiology report summarization. The processor 104 and/or server may access and implement the code stored in memory 106. The memory 106 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 106 is part of the medical imaging device 110, part of a database, part of another system, a picture archival memory, or a stand-alone device. The memory 106 may store radiology report data, including training data for configuring the automatic summarization system. The memory 106 may store an instruction set or computer code configured to implement the network.

The memory 106 includes an instruction set or computer code for implementing the networks/components of the automatic summarization system including the word extraction network 212, the sentence extraction network 210, the cnet 216, the critic, and any other component. In an embodiment, the memory 106 includes a trained network and training data. In an embodiment, only the trained network is stored in memory 106. The trained network may be configured to input the findings section of a radiology report and output a concise summarization. The memory 106 or other memory is alternatively or additionally a non-transitory computer readable storage medium storing data representing instructions executable by the programmed processor for generating resolution independent segmented data. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor 104 or processing strategy and may be performed by software, hardware, integrated circuits, firmware, micro code, and the like, operating alone, or in combination. Likewise, processing strategies may include multiprocessing, multitasking, parallel processing, and the like.

The automatic summarization system includes at least two extractor networks, an abstractor network 214, and a communication channel (cnct 216). The configuration is referred to as DiMAC or differential multi-agent actor-critic. The automatic summarization system is configured to input the FINDINGS section of the radiology report and output a concise IMPRESSION section. In an embodiment, the automatic summarization system includes a word extraction network 212, that includes a BiLSTM. The BiLSTM generates representations for words in FINDINGS. A CNN is run on concatenated word vectors to obtain FINDINGS sentence representation. The CNN-based sentence representations provide context vectors that are used as the sentence extractor inputs. The sentence extractor, for example including a LSTM based pointer extractor, selects a source sentence index at each step of decoding. Two LSTM-based pointer Extractors (part of the word and sentence networks) select a source word and sentence index at each decoding step respectively. The decision on whether word or sentence extractor output is set to empty is based on a switch probability. In addition, context vectors are shared between extractors. The abstractor network 214 then condenses each selected sentence to a concise summary. The automatic summarization system is trained/configured as described above in FIG. 5. The training process uses a RL mechanism that computes rewards for each action performed by the respective networks and updates each of them based thereon. For example, for each decoding step a sentence reward (ROUGE unigram recall) is computed between the abstract summary and a ground-truth IMPRESSIONS sentence. The training process makes use of a critic network (for example, an LSTM network) that runs for the same number of steps as the extraction networks and estimates gradients to train them respectively. MARL may be used for the coordination between the word and sentence extractors. In an embodiment, the Critic estimates the value function by not conditioning on the actions of other agents. Communication is provided by a communicator (cnct 216) that coordinates actors through message passing. As a result of the DiMAC mechanisms, gradients flow between actors during backpropagation and provide richer training signals that minimizes the learning effort.

In an embodiment, the Differential Multi-agent Actor-Critic (DiMAC) Reinforcement learning of two-step abstractive summarization model includes pre-trained sentence 210 and word extractors 212 as the actors. The action space at each step of decoding includes extracting a salient sentence and salient word for sentence 210 and word 212 extractor agents respectively. Owing to the communication between words and sentence agents in DiMAC training, there is a strong relationship between generated words and sentences. More specifically, sentences with many salient words are more likely to get extracted, and thereby yielding meaningful impression of the findings after the abstractor rewrites the extracted finding sentences. A connection network, cnct 216, is used to pass messages between the two agents. The actors' actions at the previous step is fed to cnct and a sigmoidal, mt, is obtained. Value mt is fed to sentence agent 210 while 1−mt is fed to word agent 212. As gradient term for mt flow between agents during backpropagation, it provides richer training signal, and thereby minimizing the learning effort. After an agent selects an action a reward will be given to it based on an individual reward function designed specific to the agent. In case of the sentence actor 210, a sentence reward SentR is computed using Rlr (ROUGE L recall) by comparing extracted and condensed sentences with ground truths. In case of the word actor 212, WordR is computed by checking if extracted word is in a given set of keywords. If present, WordR is unit, else it is zero. Additionally, in a multi-agent cooperative setting, joint actions of agents eventually generate a global reward. In order to let an agent deduce its contribution for overall success, a global reward is used. The global reward is computed after the agents terminate. It is composed of SentR over all exacted sentences and WordR over all extracted keywords. A centralized critic is used to estimate the gradient to train both of the actors. As learning is centralized, the critic can condition on all of multi-agents' actions and states, contrarily individual actor conditioning only on its action and state. The critic estimates a value function which is used to compute the policy gradient of an agent.

At act A230, the DiMAC system outputs a concise summary of the FINDINGS section of the radiology report. At act A240, the concise summary is provided to a user, for example, using the display 102. The display 102 is a CRT, LCD, projector, plasma, printer, tablet, smart phone or other now known or later developed display device for displaying the radiology report including the generated concise summary.

The automatic summarization system provides a combined approach with a two-step RL-based summarization task (extractive-then-abstractive). This approach is a MARL (rather than the traditional single-agent RL) which includes a new agent that extracts salient keywords from the source text and collaborates with an agent that extracts salient sentences. The system uses a Differentiable Multi-agent Actor-Critic (DiMAC) learning method for independent agents communicating via a dedicated channel. When applied to radiology reports, the results indicate, based on automatic and human expert evaluations, that the DiMAC summarization system outperforms existing baseline models for text summarization. The summarization system generates the IMPRESSIONS to reflect human-level inference and actionable information (e.g., salient sentences and keywords) towards supporting improved workflow efficiency and better-informed clinical diagnosis based on medical imaging findings.

It is to be understood that the elements and features recited in the appended claims may be combined in different ways to produce new claims that likewise fall within the scope of the present invention. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

What is claimed is:

1. A system for multi-step radiology report summarization, the system comprising:
a word extraction network configured to extract one or more words from a radiology report;

a sentence extraction network configured to extract one or more salient sentences from the radiology report based at least in part on the extracted one or more words; and an abstractor network configured to condense one or more of the one or more extracted salient sentences into a concise summary of the radiology report;

wherein the word extraction network, the sentence extraction network, and the abstractor network are trained end to end using at least a critic and a communication channel, wherein the critic is configured to estimate a value function that is used to compute a policy gradient for the word extraction network and the sentence extraction network, and the communication channel is configured to pass gradient information between the word extraction network and the sentence extraction network.

2. The system of claim 1, wherein the word extraction network and the sentence extraction network comprise a bi-directional LSTM based word encoder and a bi-directional LSTM sentence encoder respectively; wherein the bi-directional LSTM based word encoder is configured to obtain word representations from a FINDINGS portion of the radiology report and the bi-directional LSTM sentence encoder is configured to obtain sentence representations.

3. The system of claim 1, wherein the abstractor network comprises a pointer generator network.

4. The system of claim 1, wherein during training, the word extraction network and sentence extraction network are configured using multiple agent reinforcement learning.

5. The system of claim 1, wherein during training, the word extraction network and sentence extraction network actions at a previous step are input into the communication channel that generates a sigmoidal, mt, that is input into the sentence extraction network, wherein 1−mt is input into the word extraction network.

6. The system of claim 1, wherein during training, when the word extraction network or the sentence extraction network selects an action, a reward is provided to the word extraction network or the sentence extraction network to it based on an individual reward function computed specifically for either the word extraction network or the sentence extraction network.

7. The system of claim 6, wherein the reward for the sentence extraction network is computed using ROUGE L recall by comparing extracted salient sentences and condensed salient sentences with ground truth data.

8. The system of claim 6, wherein the reward for the word extraction network is computed by checking if an extracted word is in a given set of keywords.

9. The system of claim 1, further comprising an output interface configured to provide the concise summary to a user.

10. A method for configuring a system for multi-step radiology report summarization, wherein the system comprises at least a sentence extraction network, a word extraction network, a critic network, and a communication channel, the method comprising:

inputting training data from a FINDINGS section of a radiology report to the sentence extraction network and the word extraction network;

computing states for the sentence extraction network, the word extraction network, and the critic network;

sampling actions by the sentence extraction network and the word extraction network;

computing rewards based on the actions and the states; and updating the sentence extraction network, the word extraction network, and the critic network based on the computed rewards.

11. The method of claim 10, wherein inputting, computing, sampling, computing, and updating is iteratively performed for a plurality of iterations.

12. The method of claim 11, wherein when sampling actions by the sentence extraction network and the word extraction network, only one of the sentence extraction network or the word extraction network is active while the other is paused.

13. The method of claim 10, wherein each of the sentence extraction network and the word extraction network selects one of its actions and communicates with the other respective network at every step.

14. The method of claim 10, wherein the communication channel is configured to generate a sigmoidal, mt, that is input into the sentence extraction network wherein 1−mt is input into the word extraction network.

15. The method of claim 10, wherein the word extraction network is configured to extract one or more words from the FINDINGS section based on a list of keywords.

16. The method of claim 15, wherein the sentence extraction network is configured to extract one or more sentences from the FINDINGS section based in part on the extracted one or more words.

17. A method for automatic summarization of a FINDINGS section of a radiology report, the method comprising:

acquiring a radiology report that describes results of a medical procedure;

inputting the FINDINGS section of the radiology report into an automatic summarization system comprising at least a word extraction network, a sentence extraction network, a communications channel, and an abstractor, wherein the automatic summarization system is trained using differential Multi-agent Actor-Critic reinforcement learning;

outputting, by the automatic summarization system, an IMPRESSIONS section for the radiology report; and providing the IMPRESSIONS section to a user.

18. The method of claim 17, wherein the word extraction network is configured to extract one or more words from the FINDINGS section based on a list of keywords.

19. The method of claim 18, wherein the sentence extraction network is configured to extract one or more sentences from the FINDINGS section based in part on the extracted one or more words.

20. The method of claim 17, wherein the communications channel is configured to pass information between the word extraction network and the sentence extraction network.

* * * * *